(12) United States Patent
More

(10) Patent No.: US 7,775,365 B1
(45) Date of Patent: Aug. 17, 2010

(54) PROSTHETIC LIMB ASSISTANCE KIT

(76) Inventor: Robert More, P.O. Box 4546, Crestline, CA (US) 92325

( * ) Notice: Subject to any disclaimer, the term of this patent is extended or adjusted under 35 U.S.C. 154(b) by 201 days.

(21) Appl. No.: 12/189,621

(22) Filed: Aug. 11, 2008

(51) Int. Cl.
*B65D 69/00* (2006.01)

(52) U.S. Cl. .................. 206/572; 206/523; 206/764

(58) Field of Classification Search ......... 206/570–572, 206/523, 524, 363, 438, 591, 592, 594, 564, 206/754, 755, 759, 764
See application file for complete search history.

(56) References Cited

U.S. PATENT DOCUMENTS

| | | | |
|---|---|---|---|
| 2,666,927 A | 1/1954 | Morheiser | |
| 3,181,693 A * | 5/1965 | Freistat | 206/523 |
| 3,653,567 A | 4/1972 | Selvaggio | |
| 4,288,066 A | 9/1981 | Treace | |
| 4,294,349 A * | 10/1981 | Ibsen et al. | 206/523 |
| 5,207,303 A | 5/1993 | Oswalt et al. | |
| 5,593,453 A | 1/1997 | Ahlert | |
| 5,794,773 A * | 8/1998 | Moyer | 206/523 |
| 6,793,682 B1 | 9/2004 | Mantelmacher | |
| 7,568,301 B1 * | 8/2009 | Zemlansky et al. | 206/759 |
| 2006/0289329 A1 | 12/2006 | Miller | |
| 2007/0027556 A1 | 2/2007 | Wilson | |

* cited by examiner

*Primary Examiner*—Luan K Bui
(74) *Attorney, Agent, or Firm*—Crossley Patent Law; Mark A. Crossley

(57) ABSTRACT

A prosthetic limb assistance kit that is used as a maintenance kit and carrying case for prosthetic limb users to house and have readily available necessary prosthesis supplies, which include adjustment tools, replaceable prosthesis components, socks, ointments, powders, cleaning devices, and other related items. The kit comes in a carrying case and also includes a cutout area for a umbrella-like stand, which allows for air drying of a prosthesis liner worn by an individual. The stand also allows the liner from sticking to itself when it is placed in the carrying case.

8 Claims, 6 Drawing Sheets

PROSTHETIC LIMB ASSISTANCE KIT

BACKGROUND OF THE INVENTION

The present invention concerns that of a new and improved prosthetic limb assistance kit that is used as a maintenance kit and carrying case for prosthetic limb users to house and have readily available necessary prosthesis supplies.

SUMMARY OF THE INVENTION

The present invention concerns that of a new and improved prosthetic limb assistance kit that is used as a maintenance kit and carrying case for prosthetic limb users to house and have readily available necessary prosthesis supplies, which include adjustment tools, replaceable prosthesis components, socks, ointments, powders, cleaning devices, and other related items. The kit comes in a carrying case and also includes a cutout area for a umbrella-like stand, which allows for air drying of a prosthesis liner worn by an individual. The stand also allows the liner from sticking to itself when it is placed in the carrying case.

There has thus been outlined, rather broadly, the more important features of a prosthetic limb assistance kit that the detailed description thereof that follows may be better understood and in order that the present contribution to the art may be better appreciated. There are, of course, additional features of the prosthetic limb assistance kit that will be described hereinafter and which will form the subject matter of the claims appended hereto.

In this respect, before explaining at least one embodiment of the prosthetic limb assistance kit in detail, it is to be understood that the prosthetic limb assistance kit is not limited in its application to the details of construction and to the arrangements of the components set forth in the following description or illustrated in the drawings. The prosthetic limb assistance kit is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present prosthetic limb assistance kit. It is important, therefore, that the claims be regarded as including such equivalent constructions insofar as they do not depart from the spirit and scope of the present invention.

It is therefore an object of the present invention to provide a prosthetic limb assistance kit which has all of the advantages of the prior art and none of the disadvantages.

It is another object of the present invention to provide a prosthetic limb assistance kit which may be easily and efficiently manufactured and marketed.

It is another object of the present invention to provide a prosthetic limb assistance kit which is of durable and reliable construction.

It is yet another object of the present invention to provide a prosthetic limb assistance kit which is economically affordable and available for relevant market segment of the purchasing public.

Other objects, features and advantages of the present invention will become more readily apparent from the following detailed description of the preferred embodiment when considered with the attached drawings and appended claims.

DESCRIPTION OF THE PREFERRED EMBODIMENT

Figure 1:
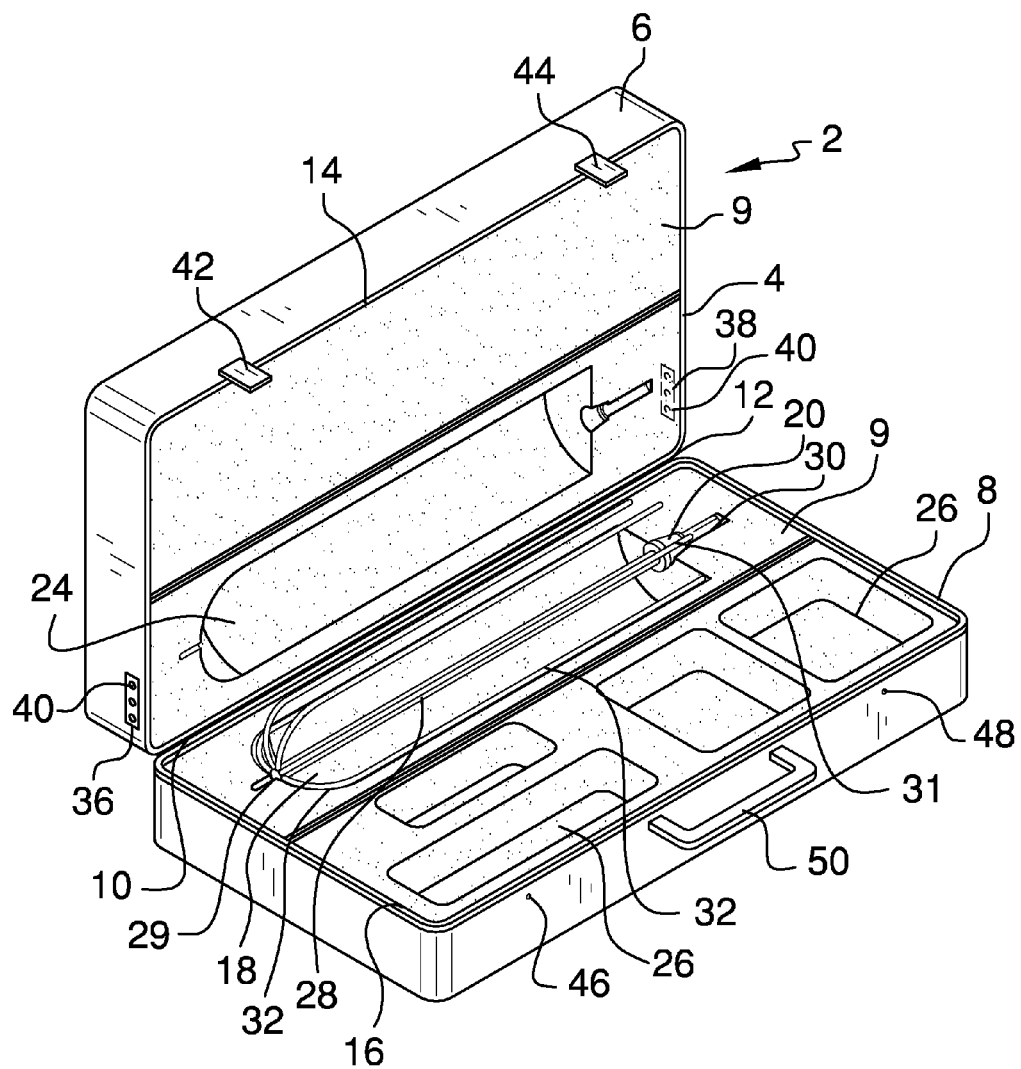
FIG. 1 shows a front perspective view of the prosthetic limb assistance kit when the carrying case is in an open position.
Figure 2:
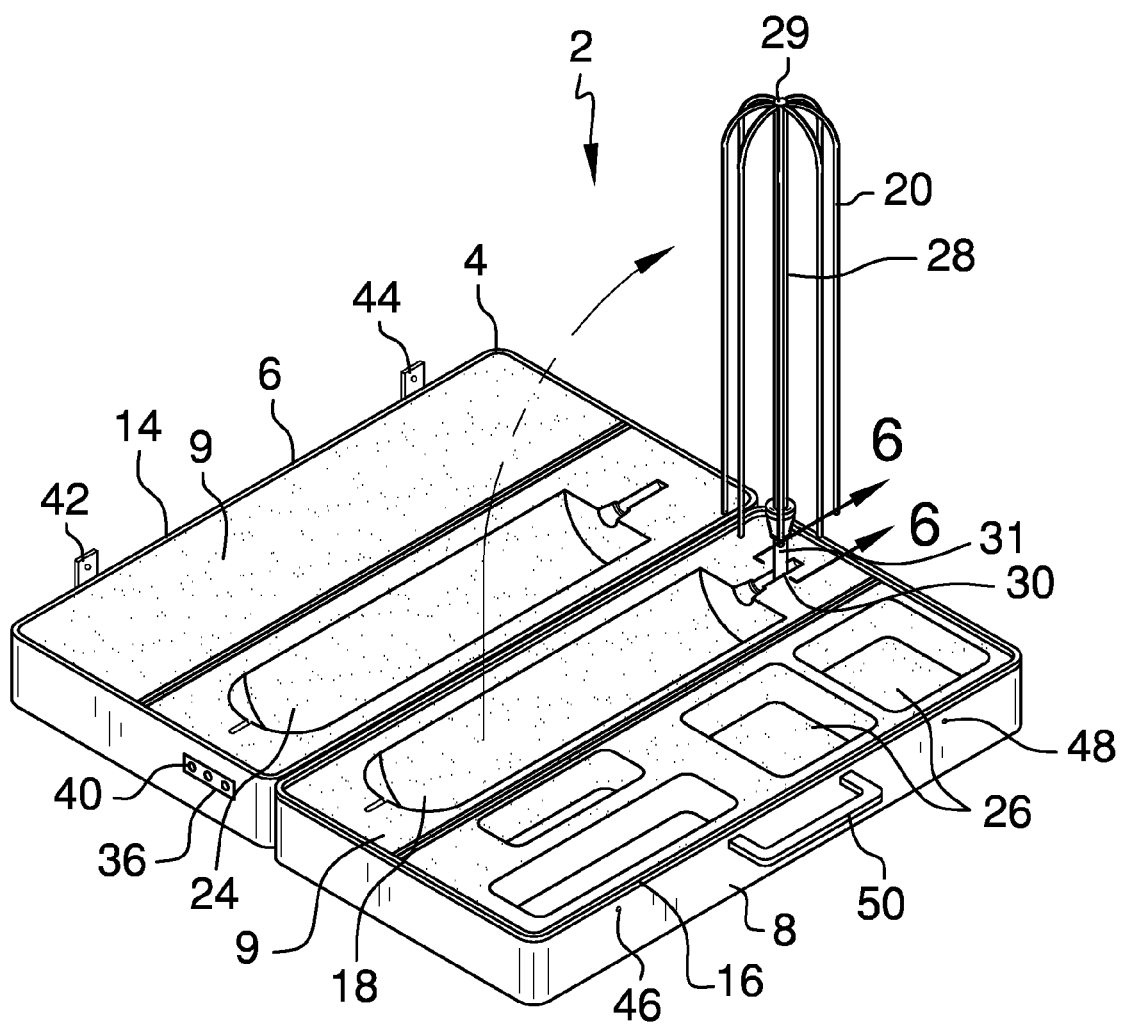
FIG. 2 shows a front perspective view of the prosthetic limb assistance kit when the carrying case is in an open position and the included stand is placed in a vertical position.
Figure 3:
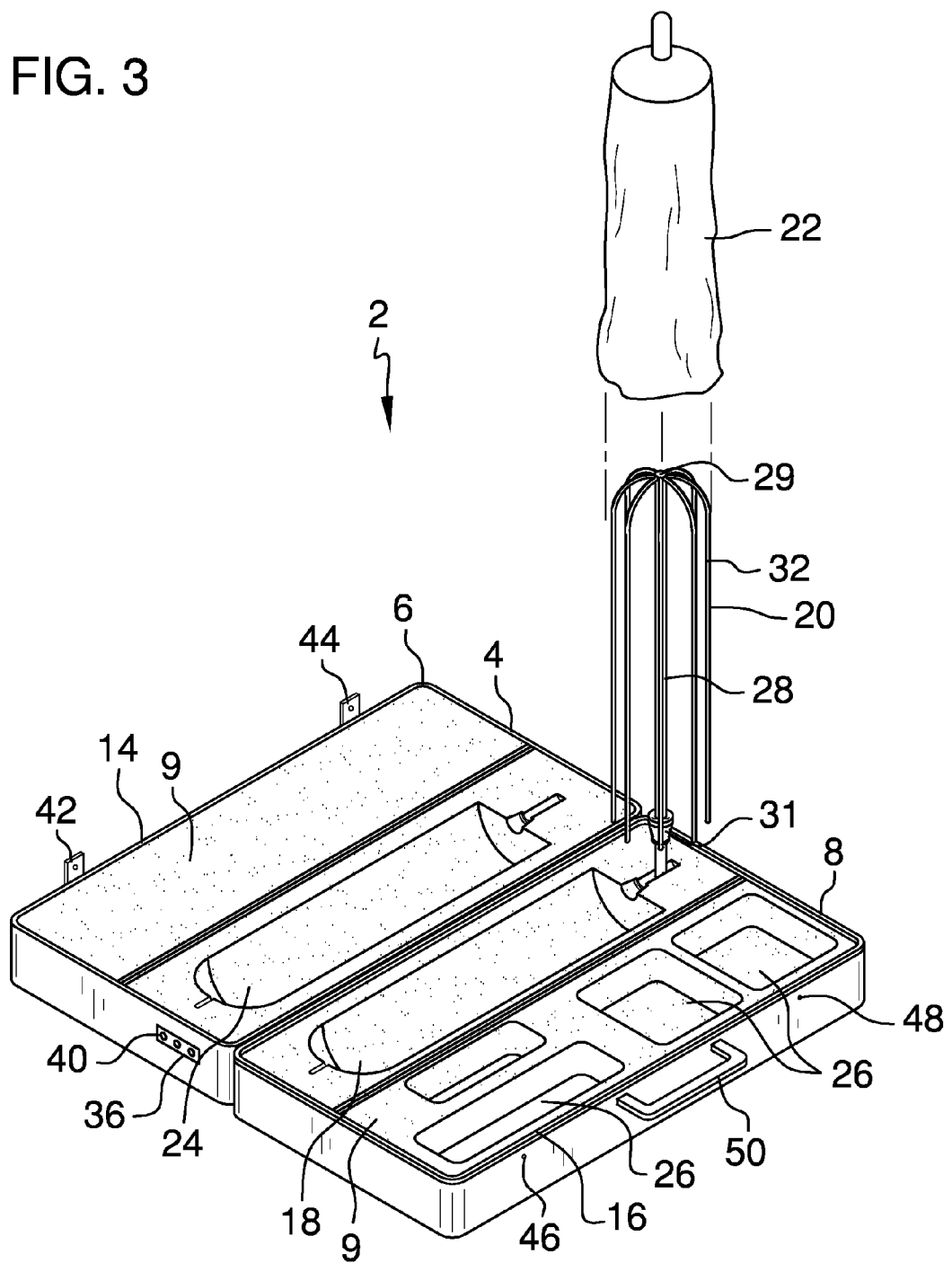
FIG. 3 shows a front perspective view of the prosthetic limb assistance kit when the carrying case is in an open position, the included stand is placed in a vertical position, and a prosthetic limb cover is being placed over the stand.
Figure 4:
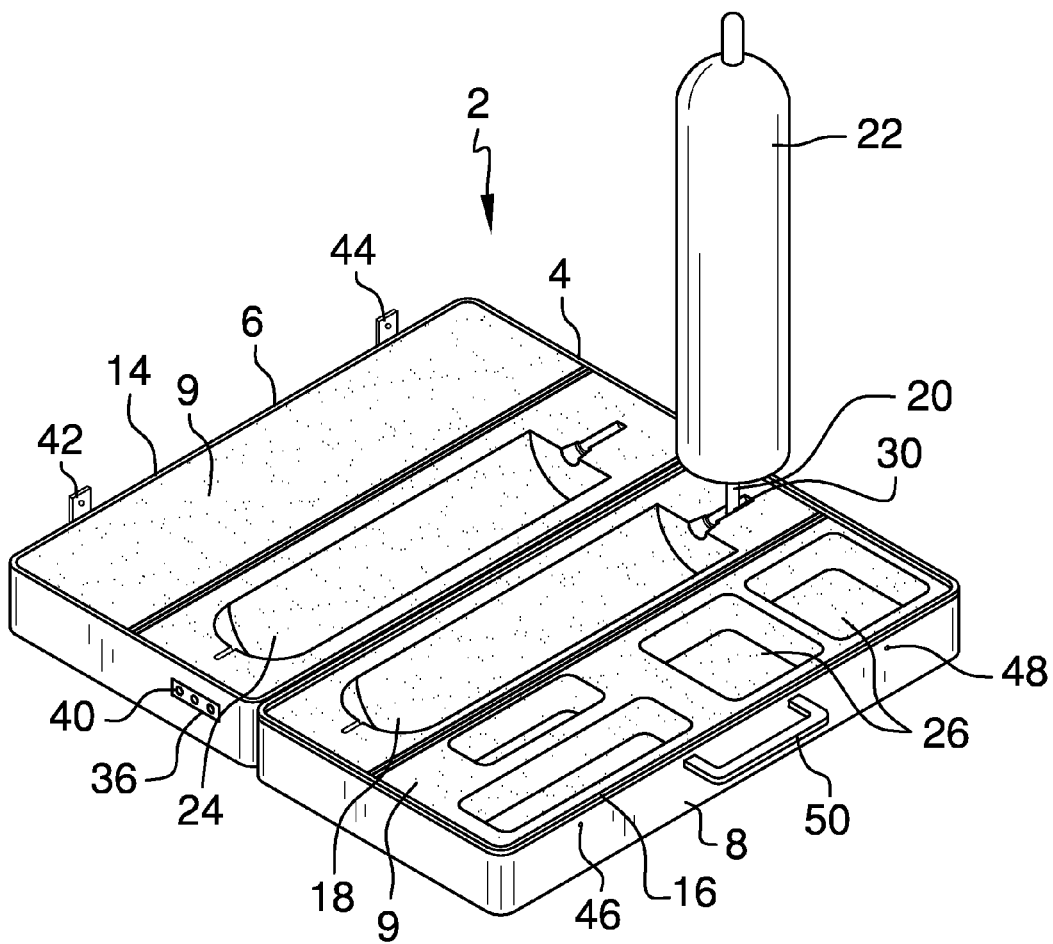
FIG. 4 shows a front perspective view of the prosthetic limb assistance kit when the carrying case is in an open position, the included stand is placed in a vertical position, and a prosthetic limb cover has been placed over the stand.
Figure 5:
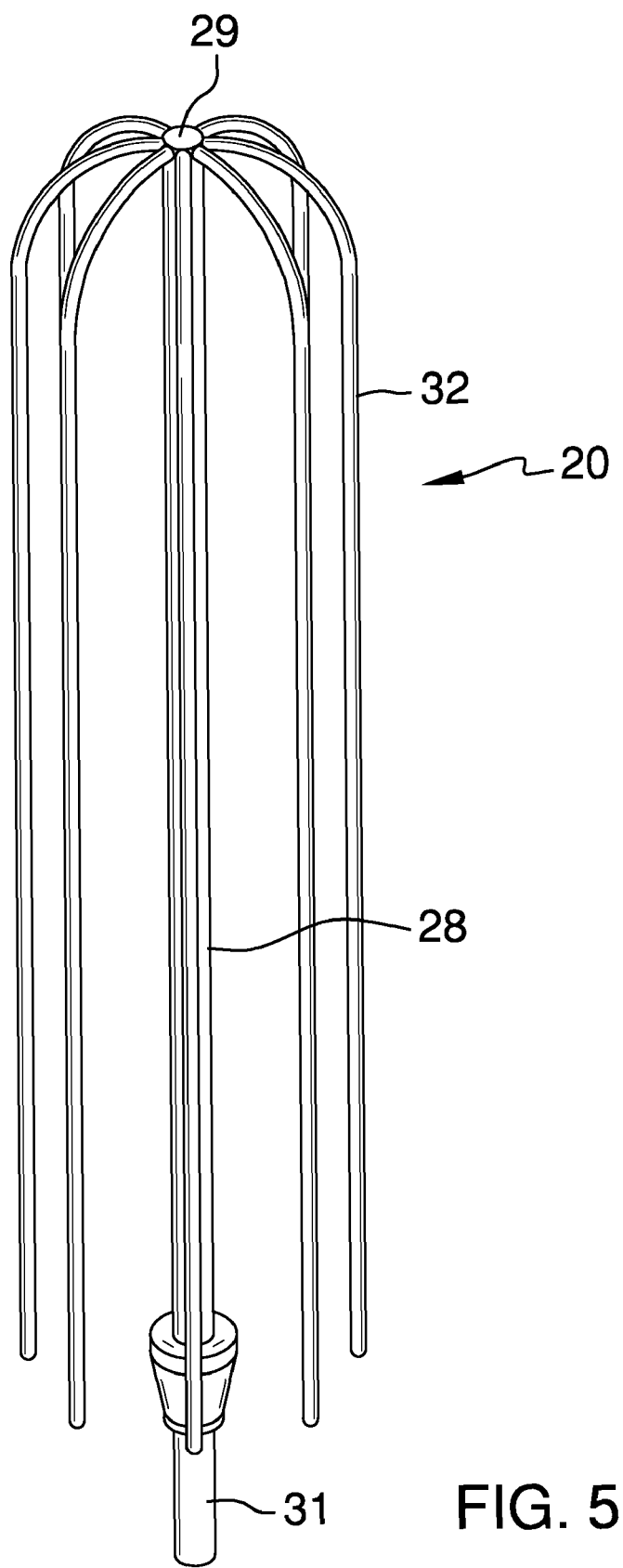
FIG. 5 shows a front view of the included stand after it has been placed in a vertical position.
Figure 6:
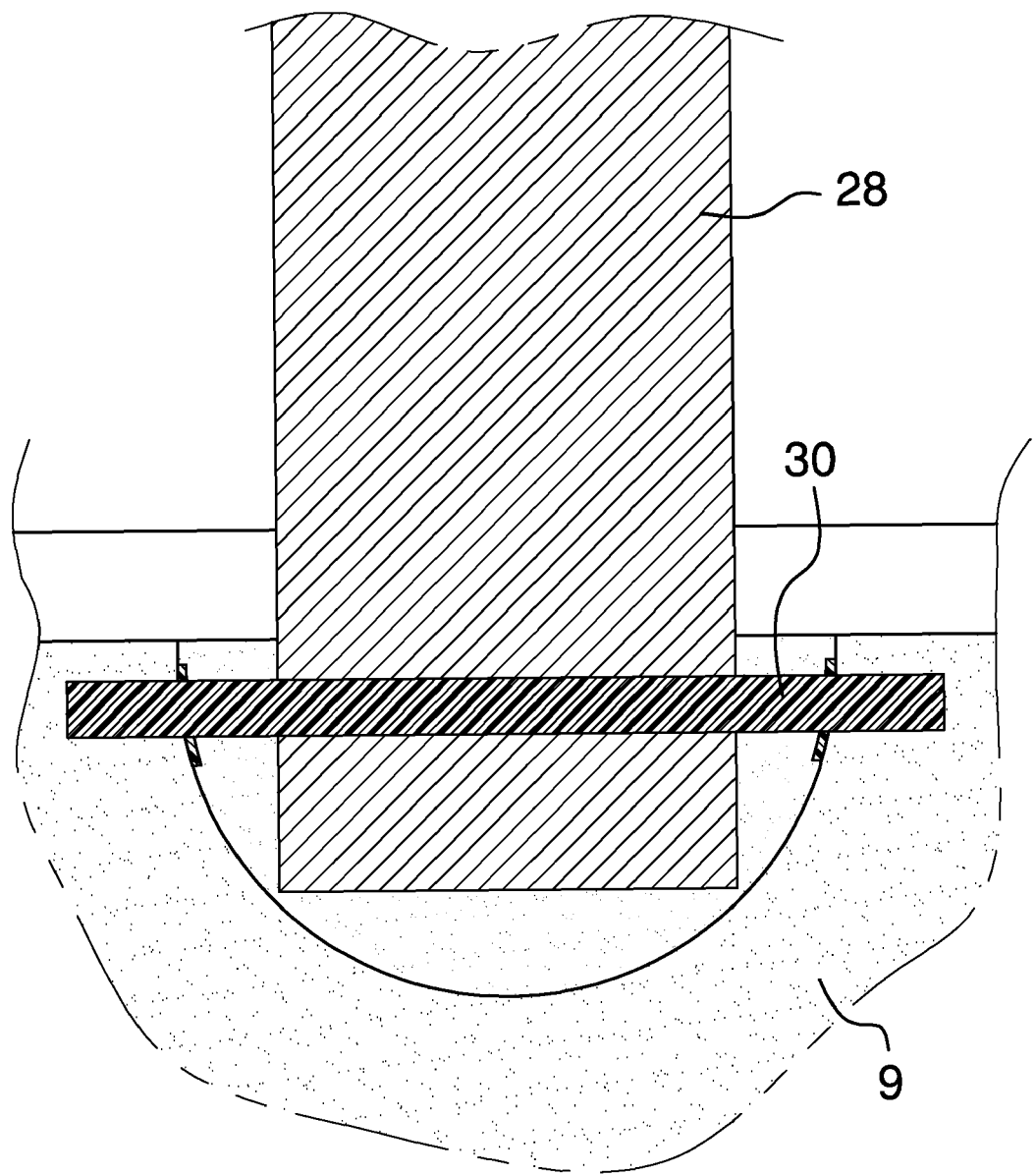
FIG. 6 shows a front view of the base of the included stand, highlighting how the included stand is mounted within the carrying case in a vertical position.

With reference now to the drawings, and in particular to FIGS. 1 through 6 thereof, a prosthetic limb assistance kit embodying the principles and concepts of the present invention and generally designated by the reference numeral 2 will be described.

As best illustrated in FIGS. 1 through 6, the prosthetic limb assistance kit 2 comprises a carrying case 4 has two portions comprising an upper portion 6 and a lower portion 8. The upper portion 6 and the lower portion 8 of the carrying case 4 are pivotally attached to one another through the use of a pair of hinges 10 and 12.

The carrying case 4 can have a wide variety of dimensions. However, the preferred dimensions of carrying case 4 are approximately twenty-six inches in length, fourteen inches in height, and at least several inches in thickness when the upper portion 6 and lower portion 8 would be placed against one another.

Both the upper portion 6 and the lower portion 8 of the carrying case 4 have their own airtight seals 14 and 16, respectively. Each of these seals, when placed against one another, will prevent dirt, debris, moisture, and other objects from getting in the carrying case 4 when the carrying case 4 is in a closed position. This characteristic is essential to protect various components placed within the carrying case 4, as these components can typically be very expensive to replace should this need arise.

The upper portion 6 and the lower portion 8 of the carrying case 4 each have an amount of foam padding 9 within them. The lower portion 8 of the carrying case 4 has a cutout area 18 in the foam padding 9 which a stand 20 is located within. The stand 20 is designed to allow for the air drying of the prosthesis liner 22 that is worn by an individual in conjunction with the prosthesis itself. The upper portion 6 of the carrying case 4 has a cutout area 24 in the foam padding 9 that matches up with the cutout area 18 in the lower portion 8 of the carrying case 4 to properly close up the stand 20.

The lower portion 8 of the carrying case has a plurality of additional cutout compartments 26, with these compartments 26 designed to house needed items such as adjustment tools, components, socks, ointments, lubricants, powders, cleaning supplies, and related items.

The stand 20 itself has a central support pole 28, which has two ends comprising an upper end 29 and a lower end 31. The lower end 31 of the central support pole 28 is pivotally attached to a pivot pin 30 within the carrying case 4. A plurality of outer support poles 32 are attached to the upper end 29 of the central support pole 28 by branching out and then down from the upper end 29 of the central support pole 28. The number of outer support poles 32 preferably numbers either six or eight outer support poles 32 and they are evenly dispersed in their angular positions as they come off of and then down from the top of the central support pole 28. Each of the outer support poles 32 is in a fixed position relative to the central support pole 28.

In use, a prosthetic limb cover 22 can be placed over the outer support poles 32 and then pulled downward so it completely envelops the outer support poles 32 over the central support pole 28. The stand 20 can either then be left in this position, or alternatively, can be folded back into its cutout area 18 within the lower portion 8 of the carrying case 4. The carrying case 4 can then be shut and the prosthetic limb assistance kit 2 can be transported as needed.

While in transport, the prosthetic limb cover 22 will receive continued aeration from a pair of vent units 36 and 38 that are located on the upper portion 6 of the carrying case 4. Each of the vent units 36 and 38 has a plurality of holes 40 and connects the outside air to the air located within the cutout area 18 of the lower portion 8 and the cutout area 24 within the upper portion 6 of the carrying case 4.

When closed, the upper portion 6 has a pair of latches 42 and 44 that are capable of being removably connected to nails 46 and 48, which are located on lower portion 8. Furthermore, the kit 2 has a handle 50 attached to the lower portion 8, allowing an individual to easily transport the carrying case 4 of the kit 2 as needed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A prosthetic limb assistance kit comprising
    a carrying case, the carrying case comprising two portions comprising an upper portion and a lower portion,
    an amount of padding within the upper portion and the lower portion,
    means for pivotally attaching the upper portion of the carrying case to the lower portion of the carrying case,
    a stand,
    means for placing the stand within the carrying case,
    means for sealing up the carrying case once the carrying case has been closed,
    wherein the means for pivotally attaching the upper portion of the carrying case to the lower portion of the carrying case further comprises
        a pair of hinges comprising a first hinge and a second hinge,
        wherein each hinge of the pair of hinges is attached to the lower portion of the carrying case,
        further wherein each hinge of the pair of hinges is attached to the upper portion of the carrying case,
    wherein the means for placing the stand within the carrying case further comprises
        a first cutout area located within the lower portion of the carrying case,
        a second cutout area located within the upper portion of the carrying case,
        means for providing external aeration to the first cutout area and the second cutout area,
        wherein the first cutout area matches up with the second cutout area when the lower portion and the upper portion of the carrying case are closed and pressed up against one another.

2. A prosthetic limb assistance kit according to claim 1 wherein the stand further comprises
    (a) a central support pole, the central support pole having two ends comprising an upper end and a lower end,
    (b) a plurality of outer support poles attached to the upper end of the central support pole,
    (c) means for pivotally attaching the central support pole to the lower portion of the carrying case,
    (d) wherein each of the outer support poles of the plurality of outer support poles branches out away from the upper end of the central support pole, further wherein each outer support pole of the plurality of outer support poles then branches down from the upper end of the central support pole.

3. A prosthetic limb assistance kit according to claim 2 wherein the means for pivotally attaching the central support pole to the lower portion of the carrying case further comprises
    (a) a pivot pin located in the lower portion of the carrying case,
    (b) wherein the lower end of the central support pole is attached to the pivot pin.

4. A prosthetic limb assistance kit according to claim 3 wherein the means for sealing up the carrying case once the carrying case has been closed further comprises
    (a) a first airtight seal located on the upper portion of the carrying case,
    (b) a second airtight seal located on the lower portion of the carrying case,
    (c) wherein the first airtight seal is placed against the second airtight seal when the lower portion and the upper portion of the carrying case are placed against one another.

5. A prosthetic limb assistance kit according to claim 4 wherein the means for providing external aeration to the first cutout area and the second cutout area further comprises
    (a) a pair of vent units comprising a first vent unit and second vent unit, wherein each of the vent units is located on the upper portion of the carrying case,
    (b) a plurality of holes located on each vent unit of the pair of vent units,
    (c) wherein each of the vent units connects outside air to the area located within the cutout area within the lower portion and the cutout area within the upper portion of the carrying case.

6. A prosthetic limb assistance kit according to claim 5 wherein the kit further comprises a means for closing the carrying case, the means further comprising
    (a) a pair of latches comprising a first latch and a second latch, wherein each latch of the pair of latches is attached to the upper portion of the carrying case, (b) a pair of nails comprising a first nail and a second nail, wherein each nail of the pair of nails is attached to the lower portion of the carrying case, (c) wherein each of the latches of the pair of latches is removably connected to a nail of the pair of nails when the carrying case is closed.

7. A prosthetic limb assistance kit according to claim 6 wherein the kit further comprises (a) a handle, (b) wherein the handle is attached to the lower portion of the carrying case.

8. A prosthetic limb assistance kit comprising (a) a carrying case, the carrying case comprising two portions comprising an upper portion and a lower portion, (b) an amount of padding within the upper portion and the lower portion, (c) means for pivotally attaching the upper portion of the carrying case to the lower portion of the carrying case, said means further comprising (i) a pair of hinges comprising a first hinge and a second hinge, (ii) wherein each hinge of the pair of hinges is attached to the lower portion of the carrying case, (iii) further wherein each hinge of the pair of hinges is attached to the upper portion of the carrying case, (d) a stand, the stand further comprising (i) a central support pole, the central support pole having two ends comprising an upper end and a lower end, (ii) a plurality of outer support poles attached to the upper end of the central support pole, (iii) means for pivotally attaching the central support pole to the lower portion of the carrying case, said means further comprising (1) a pivot pin located in the lower portion of the carrying case, (2) wherein the lower end of the central support pole is attached to the pivot pin (iv) wherein each of the outer support poles of the plurality of outer support poles branches out away from the upper end of the central support pole, further wherein each outer support pole of the plurality of outer support poles then branches down from the upper end of the central support pole, (e) means for placing the stand within the carrying case, said means further comprising (i) a first cutout area located within the lower portion of the carrying case, (ii) a second cutout area located within the upper portion of the carrying case, (iii) means for providing external aeration to the first cutout area and the second cutout area, said means further comprising (1) a pair of vent units comprising a first vent unit and second vent unit, wherein each of the vent units is located on the upper portion of the carrying case, (2) a plurality of holes located on each vent unit of the pair of vent units, (3) wherein each of the vent units connects outside air to the area located within the cutout area within the lower portion and the cutout area within the upper portion of the carrying case (iv) wherein the first cutout area matches up with the second cutout area when the lower portion and the upper portion of the carrying case are closed and pressed up against one another, and (f) means for sealing up the carrying case once the carrying case has been closed, said means further comprising (i) a first airtight seal located on the upper portion of the carrying case, (ii) a second airtight seal located on the lower portion of the carrying case, (iii) wherein the first airtight seal is placed against the second airtight seal when the lower portion and the upper portion of the carrying case are placed against one another, (g) means for closing the carrying case, the means further comprising (i) a pair of latches comprising a first latch and a second latch, wherein each latch of the pair of latches is attached to the upper portion of the carrying case, (ii) a pair of nails comprising a first nail and a second nail, wherein each nail of the pair of nails is attached to the lower portion of the carrying case, (iii) wherein each of the latches of the pair of latches is removably connected to a nail of the pair of nails when the carrying case is closed, (h) a handle, wherein the handle is attached to the lower portion of the carrying case.

* * * * *